United States Patent
Mauger et al.

(10) Patent No.: US 12,064,364 B2
(45) Date of Patent: Aug. 20, 2024

(54) CATHETER BASED METHODS AND DEVICES FOR OBSTRUCTIVE BLOOD FLOW RESTRICTION

(71) Applicant: NANOSTRUCTURES, INC., Santa Clara, CA (US)

(72) Inventors: Philip Mauger, Santa Clara, CA (US); Dubravka Markovic, Carlsbad, CA (US)

(73) Assignee: Nanostructures, Inc., Santa Clara, CA (US)

( * ) Notice: Subject to any disclaimer, the term of this patent is extended or adjusted under 35 U.S.C. 154(b) by 387 days.

(21) Appl. No.: 17/276,761

(22) PCT Filed: Sep. 16, 2019

(86) PCT No.: PCT/US2019/051327
§ 371 (c)(1),
(2) Date: Mar. 16, 2021

(87) PCT Pub. No.: WO2020/060932
PCT Pub. Date: Mar. 26, 2020

(65) Prior Publication Data
US 2021/0346184 A1 Nov. 11, 2021

Related U.S. Application Data

(60) Provisional application No. 62/732,706, filed on Sep. 18, 2018.

(51) Int. Cl.
*A61F 2/01* (2006.01)
*A61B 17/12* (2006.01)
(Continued)

(52) U.S. Cl.
CPC ...... *A61F 5/0079* (2013.01); *A61B 17/12036* (2013.01); *A61F 2/01* (2013.01); *A61F 2/90* (2013.01); *A61F 2002/068* (2013.01)

(58) Field of Classification Search
CPC .. A61F 2/90; A61F 2/01; A61F 5/0079; A61F 2002/068; A61B 17/12036
See application file for complete search history.

(56) References Cited

U.S. PATENT DOCUMENTS

| 5,263,964 A | 11/1993 | Purdy |
| 5,304,195 A | 4/1994 | Twyford et al. |

(Continued)

FOREIGN PATENT DOCUMENTS

| CN | 102202585 | 9/2011 |
| CN | 105142545 | 12/2015 |

(Continued)

OTHER PUBLICATIONS

Patent Cooperation Treaty, International Search Report and Written Opinion, Application No. PCT/US2019/051327, dated Jan. 22, 2020, in 12 pages.

*Primary Examiner* — Dinah Baria
(74) *Attorney, Agent, or Firm* — Knobbe Martens Olson & Bear, LLP

(57) ABSTRACT

The present disclosure relates to an implantable device having a frame and a flow restrictor. The frame includes a central portion and an end portion on either end of the frame. The flow restrictor is disposed within a lumen of the frame. The flow restrictor is configured to transition between a collapsed configuration and a deployed configuration. The flow restrictor may include a porosity configured to reduce fluid flow through the flow restrictor without completely occluding fluid flow.

15 Claims, 6 Drawing Sheets

(51) Int. Cl.
*A61F 2/90* (2013.01)
*A61F 5/00* (2006.01)
*A61F 2/06* (2013.01)

(56) References Cited

U.S. PATENT DOCUMENTS

| | | | |
|---|---|---|---|
| 5,350,397 A | 9/1994 | Palermo et al. | |
| 5,497,722 A | 3/1996 | English, Sr. | |
| 5,624,449 A | 4/1997 | Pham et al. | |
| 5,749,894 A | 5/1998 | Engelson | |
| 5,928,260 A | 7/1999 | Chin et al. | |
| 5,980,514 A | 11/1999 | Kupiecki et al. | |
| 6,036,720 A | 3/2000 | Abrams et al. | |
| 6,077,291 A | 6/2000 | Das | |
| 6,168,622 B1 | 1/2001 | Mazzocchi | |
| 6,497,722 B1 | 12/2002 | Von Oepen et al. | |
| 6,689,141 B2 | 2/2004 | Ferrera et al. | |
| 6,746,468 B1 | 6/2004 | Sepetka et al. | |
| 6,911,037 B2 | 5/2005 | Gainor et al. | |
| 7,011,094 B2 | 3/2006 | Rapacki et al. | |
| 8,142,456 B2 | 3/2012 | Rosqueta et al. | |
| 8,444,668 B2 | 5/2013 | Jones et al. | |
| 10,130,372 B2 | 11/2018 | Griffin | |
| 2001/0044634 A1 | 11/2001 | Don Michael et al. | |
| 2002/0026211 A1 | 2/2002 | Khosravi et al. | |
| 2003/0093097 A1 | 5/2003 | Avellanet et al. | |
| 2003/0171739 A1 | 9/2003 | Murphy et al. | |
| 2003/0187475 A1 | 10/2003 | Tsugita et al. | |
| 2003/0220667 A1* | 11/2003 | van der Burg | A61B 17/12022 606/200 |
| 2004/0087998 A1 | 5/2004 | Lee et al. | |
| 2004/0153025 A1 | 8/2004 | Seifert et al. | |
| 2004/0193206 A1 | 9/2004 | Gerberding et al. | |
| 2005/0277978 A1 | 12/2005 | Greenhalgh | |
| 2007/0088387 A1 | 4/2007 | Eskridge et al. | |
| 2007/0191884 A1 | 8/2007 | Eskridge et al. | |
| 2007/0265656 A1 | 11/2007 | Amplatz | |
| 2007/0270902 A1 | 11/2007 | Slazas et al. | |
| 2008/0004653 A1* | 1/2008 | Sherman | A61B 17/12022 606/195 |
| 2009/0112228 A1 | 4/2009 | Deshpande et al. | |
| 2009/0112249 A1 | 4/2009 | Miles et al. | |
| 2009/0112251 A1 | 4/2009 | Qian et al. | |
| 2009/0112253 A1 | 4/2009 | Neilan | |
| 2010/0094335 A1 | 4/2010 | Gerberding et al. | |
| 2011/0319926 A1 | 12/2011 | Becking et al. | |
| 2012/0065667 A1 | 3/2012 | Javois | |
| 2012/0095500 A1 | 4/2012 | Heuser | |
| 2012/0330341 A1 | 12/2012 | Becking et al. | |
| 2013/0116722 A1 | 5/2013 | Aboytes et al. | |
| 2013/0325053 A1 | 12/2013 | Porter et al. | |
| 2014/0288633 A1 | 9/2014 | Burke et al. | |
| 2015/0216534 A1 | 8/2015 | Riina et al. | |
| 2015/0250579 A1* | 9/2015 | Howard | A61F 2/04 623/23.7 |
| 2015/0272590 A1 | 10/2015 | Aboytes et al. | |
| 2015/0297240 A1 | 10/2015 | Divino et al. | |
| 2015/0374483 A1 | 12/2015 | Janardhan et al. | |
| 2016/0022275 A1 | 1/2016 | Garza | |
| 2016/0022445 A1 | 1/2016 | Ruvalcaba et al. | |
| 2016/0051263 A1 | 2/2016 | Morsi | |
| 2016/0113764 A1 | 4/2016 | Sheahan et al. | |
| 2016/0120551 A1 | 5/2016 | Connor | |
| 2016/0166257 A1 | 6/2016 | Wayne et al. | |
| 2016/0220265 A1 | 8/2016 | Pokorney | |
| 2016/0324668 A1 | 11/2016 | Wallace et al. | |
| 2016/0374690 A9 | 12/2016 | Connor | |
| 2017/0027552 A1 | 2/2017 | Turkington et al. | |
| 2017/0035589 A1 | 2/2017 | Carpenter et al. | |
| 2017/0119408 A1 | 5/2017 | Ma | |
| 2017/0128077 A1 | 5/2017 | Hewitt et al. | |
| 2017/0143359 A1 | 5/2017 | Nguyen et al. | |
| 2017/0156734 A1 | 6/2017 | Griffin | |
| 2017/0165046 A1 | 6/2017 | Johnson et al. | |
| 2017/0189035 A1 | 7/2017 | Porter | |
| 2017/0367710 A1 | 12/2017 | Yang | |
| 2017/0367713 A1 | 12/2017 | Greene et al. | |
| 2018/0098777 A1 | 4/2018 | Gabbay | |
| 2018/0103971 A1 | 4/2018 | Imai et al. | |
| 2018/0147041 A1 | 5/2018 | Chouinard et al. | |
| 2018/0153674 A1 | 6/2018 | Walzman | |
| 2018/0206850 A1 | 7/2018 | Wang | |
| 2018/0296224 A1 | 10/2018 | Kealey et al. | |
| 2018/0311029 A1 | 11/2018 | Hocking et al. | |
| 2019/0046343 A1 | 2/2019 | Choubey | |
| 2019/0142435 A1 | 5/2019 | DeMeritt | |
| 2019/0223876 A1 | 7/2019 | Badruddin et al. | |
| 2019/0343664 A1 | 11/2019 | Ruvalcaba et al. | |
| 2020/0323539 A1 | 10/2020 | Mauger et al. | |
| 2021/0052278 A1 | 2/2021 | Mauger et al. | |
| 2021/0275189 A9 | 9/2021 | Mauger et al. | |

FOREIGN PATENT DOCUMENTS

| | | |
|---|---|---|
| CN | 105142546 | 12/2015 |
| CN | 105007859 | 7/2018 |
| EP | 2932921 | 10/2015 |
| JP | 2017-516605 | 6/2017 |
| WO | WO 2010/28314 | 3/2010 |
| WO | WO 2013/103888 | 7/2013 |
| WO | WO 2013/142756 | 9/2013 |
| WO | WO 2014/105932 | 12/2013 |
| WO | WO 2014/145005 | 3/2014 |
| WO | WO 2014/144980 | 9/2014 |
| WO | WO 2015/123607 | 8/2015 |
| WO | WO 2016/137997 | 9/2016 |
| WO | WO 2017/106567 | 6/2017 |
| WO | WO 2017/205617 | 11/2017 |
| WO | WO 2019/152434 | 8/2019 |

* cited by examiner

CATHETER BASED METHODS AND DEVICES FOR OBSTRUCTIVE BLOOD FLOW RESTRICTION

BACKGROUND

Field

Methods and devices for achieving controlled blood flow restriction in specifically targeted regions of the vascular system for the purpose of reducing blood flow to targeted organs and tissues resulting in therapeutic benefits.

SUMMARY

The use of catheter delivered implants or surgical procedures in the vascular system is well established in current medical practice. These techniques and devices are used for example, to clean out and reinforce clogged arteries (angioplasty and stenting), for capture and retrieval of clots (mechanical thrombectomy), to block blood flow into aneurysms (embolization and flow diversion), and heart valve replacement.

Embolization procedures are types of catheter based techniques that are used to create, through the release of microspheres or other agents, blockage of the arteries leading into targeted tissue regions so as to stop hemorrhaging or induce ischemia.

There exists a therapeutic need for new devices and procedures for the purpose of restricting or reducing blood flow in a vessel but not to the extent of embolization where the blood flow may be totally blocked. Reducing blood flow to a target organ or region has the potential to modify the cellular activity of that tissue to achieve a therapeutic benefit without creating more extreme cellular damage such as would be the result of complete embolization of blood perfusion into said tissue.

One example of this therapeutic need is in the treatment of obesity. Increasing obesity rates are a serious issue worldwide in all developed societies. Obesity is a significant contributory factor in diabetes, hypertension, cardiovascular diseases, and other metabolic disorders.

Current treatments for obesity include diet, exercise, medication and, in extreme cases, bariatric surgery. One treatment is gastric bypass surgery. It involves reconnecting parts of the stomach and intestines so that food bypasses most of the stomach and the first part of the small intestine. Other methods include gastric banding and inflatable balloon devices inserted into the stomach to stretch the stomach wall and simulate satiety.

The success rates of these treatments are highly variable and the more extreme treatments such as bariatric surgery are significantly invasive, non-reversible, and prone to complications.

There is a need for effective but also minimally invasive procedures for the treatment of obesity. One pathway that has been clinically identified is the production of the Ghrelin enzyme and its response interaction with the pituitary gland. Ghrelin is an orexigenic or appetite-stimulating hormone.

Ghrelin is released primarily from the fundus (upper lobe) of the stomach when the stomach muscle is relaxed in a non-stretched state due to minimal food presence in the stomach cavity. The Ghrelin enzyme is released by the fundus to interact with the pituitary gland and initiate the chemical mechanisms for a hunger response by the individual. When the person eats, the stomach volume expands, resulting in a stretching of the fundus region and a reduction in Ghrelin levels.

This presumed mechanism is therefore correlated to the expansion and contraction of the fundus area of the stomach. The fundus is fed by the arterial vascular system. Expansion of the fundus exerts an elastic stretching force on the arteries and veins of the upper lobe of the stomach that reduces the cross-sectional area of the blood feeding arteries, thus reducing the flow and volume transfer of oxygen to the fundus glands and therefore reducing enzyme generation.

Once the Ghrelin enzyme has been produced in the fundus, it is released into the fundus veins. The coronary vein, or left vein, is one of the gastric veins in the stomach and functions to transport blood that needs oxygen. This vein moves across the stomach and up to the top opening, where the stomach meets the esophagus.

The right vein is located on the right side of the stomach, in the area known as the lesser curvature of the stomach. It pushes blood out of this area of the stomach. Both the left and right gastric veins belong to the portal circulation system. In this system blood is pushed through the liver via the hepatic portal veins, rather than pushed directly to the heart, for oxygenation.

The theory is that these veins are the carrying mechanism for the transportation of Ghrelin to the body and ultimately to the pituitary gland for the initiation of the hunger response.

Gastric artery embolization is an established procedure that is used for life-threatening hemorrhages of the gastric fundus or gastro esophageal hemorrhages that are not controllable by endoscopic intervention. Gastric arteries are embolized to stop the hemorrhaging, typically with a "gelfoam slurry." For example, FIG. 1 shows a representation of a gastric embolization procedure with embolic spheres 6 being released from a catheter 8 into arteries 4 that feed the fundus. Retrospective studies have shown that this embolization appears to induce sufficient ischemia to the mucosa of the gastric fundus to inhibit ghrelin production by the cells which, in turn, leads to weight loss.

A newly developed procedure, called bariatric arterial embolization, starts by feeding a small catheter through a patient's arteries, via an incision in either the groin or the wrist. Tiny beads, typically in the size range of 300-500 microns in diameter, are injected through the catheter and create blockage in vessels distal to the release point in order to decrease blood flow to the fundus. The procedure causes ischemia in the gastric fundus, which appears to decrease ghrelin production, resulting in appetite suppression, early satiety and weight loss.

Adverse side effects, complications, and patient population restrictions are not yet well known, but potentially include; short term gastric ulcerations, nausea, and vomiting, long term ulcer risk with the potential for non-healing, and variability in control of the specific locations in the vasculature where the injected beads create blockage thus potentially leading to incomplete ischemia in the target tissues or also ischemia in non-targeted regions.

Embolization poorly mimics the natural expansion and contraction of the gastric arteries since it simply shuts off flow and does not offer any options to controllably reduce the flow without a complete block. Controlled flow reduction is an improved alternative that may provide equivalent or superior benefit with lower rates of complication.

A second example of the need for blood flow restriction is in the treatment of uterine fibroids. Fibroid tumors, also known as myomas, are benign tumors that arise from the muscular wall of the uterus. Fibroids are the most frequently seen tumors of the female reproductive system. Possibly as many as 1 in 2 women will develop one or more fibroids in their lifetime. Many fibroids are asymptomatic and treatment is not usually needed. While it is extremely rare for them to turn cancerous, they can cause heavy menstrual bleeding, pain in the pelvic region, and pressure on the bladder or bowel. In general, the larger the fibroid, the more severe the symptoms.

Current surgical treatment options include hysterectomy or the surgical removal of the entire uterus (fibroids remain the number one reason for hysterectomies in the United States), myomectomy or the surgical removal of fibroids only leaving the uterus intact, myolysis which uses radiofrequency energy, electric current, freezing, or lasers introduced laparoscopically to destroy the fibroids and shrinks the blood vessels that feed them, and endometrial ablation where the lining of the uterus is removed or destroyed with laser, wire loops, boiling water, electric current, microwaves, freezing, and other methods.

Drug based treatments utilize Gonadotropin-releasing hormone agonists (GnRH agonists). This approach lowers levels of estrogen and triggers a "medical menopause." Sometimes GnRH agonists are used to shrink the fibroid, making surgical treatment easier. GnRH agonists typically are used for no more than three to six months because symptoms return when the medication is stopped and long-term use can cause loss of bone.

Uterine artery embolization is a treatment option where the arteries supplying blood to the fibroids are identified and then embolized. The embolization cuts off the blood supply to the fibroids, thus shrinking them. Uterine artery embolization has been available for over 20 years for the treatment of various obstetric and gynecologic conditions associated with uncontrollable vaginal hemorrhages. Embolization for the treatment of fibroids is a relatively recent adaptation of the technology. In this procedure, a catheter is introduced through the femoral artery and advanced to the uterine artery connected to the fibroid so that microspheres, typically composed of PVA, can be injected to permanently block blood flow. As in the case of bariatric arterial embolization, long term complications such as reductions in fertility or effects of ischemia of non-targeted tissue are not well known.

Since in many circumstances, it is not medically necessary to remove fibroids, but only to reduce their size or growth rate so that they become asymptomatic, ischemia is potentially not the optimum treatment. As in the case of obesity as discussed above flow reduction without ischemia may provide an alternative treatment option with less risk.

Another example of the need for blood flow restriction is in the treatment of benign prostatic hyperplasia (BPH; aka enlarged prostate). An enlarged prostate affects approximately half of men age 51 to 60 and as many as 90 percent of men older than 80. Symptoms of an enlarged prostate include but are not limited to dribbling, urinary urgency, having to urinate multiple times during the night, painful urination, and urinary frequency.

Prostatectomy (removal of the prostate) is commonly used for prostate cancer treatment, but is generally not required for BPH.

Medications for BPH treatment include alpha-blockers to relax the muscles in the prostate and the neck of the bladder so that urine flows more easily, 5-alpha reductase inhibitors to slow the growth of the prostate and cause it to shrink by altering the actions of certain male hormones, anticholinergics that can help with urge incontinence, and the phosphodiesterase 5 inhibitor tadalafil (Cialis), which can be used to treat both an enlarged prostate and erectile dysfunction. An additional drug that combines an alpha-blocker and a 5-alpha reductase inhibitor also is available.

If medications for BPH fail to keep the urethra open, then there are minimally invasive surgical treatment options. The most common procedure currently is transurethral resection of the prostate (TURP). A combined visual and surgical instrument (resectoscope) is inserted through the urethra and excess prostate tissue is removed by electrocautery or sharp dissection. Variations on this procedure can use laser, radio waves, heat, or microwaves to destroy the excess tissue.

Possible side effects associated with procedures that compromise the urethra are erectile dysfunction, urinary incontinence, and retrograde ejaculation. Longevity of the treatment and the need for retreatment can also be an issue.

Prostatic arterial embolization is a recently available treatment, similar to uterine artery embolization, where a catheter is inserted into the vasculature through the arm or groin and advanced to a position in the blood vessels adjacent to the prostate. Microspheres, typically of PVA plastic, are then released from the catheter into the blood flow. The spheres are sized to become lodged in the arteries feeding the prostate thus blocking the blood supply and causing the gland to eventually shrink.

A significant advantage of prostatic arterial embolization is the absence of both urinary incontinence and sexual side effects. Difficulties with prostate embolization are similar to other embolization treatments in that control of the exact positioning of the microspheres is not possible leading to non-targeted tissue impacts, and side effects of ischemia.

Use of flow restriction in the vascular system as an alternative to embolization is a largely unexplored therapy and so additional therapeutic applications are expected to result from the availability of devices in addition to the potential treatments indicated above.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1:
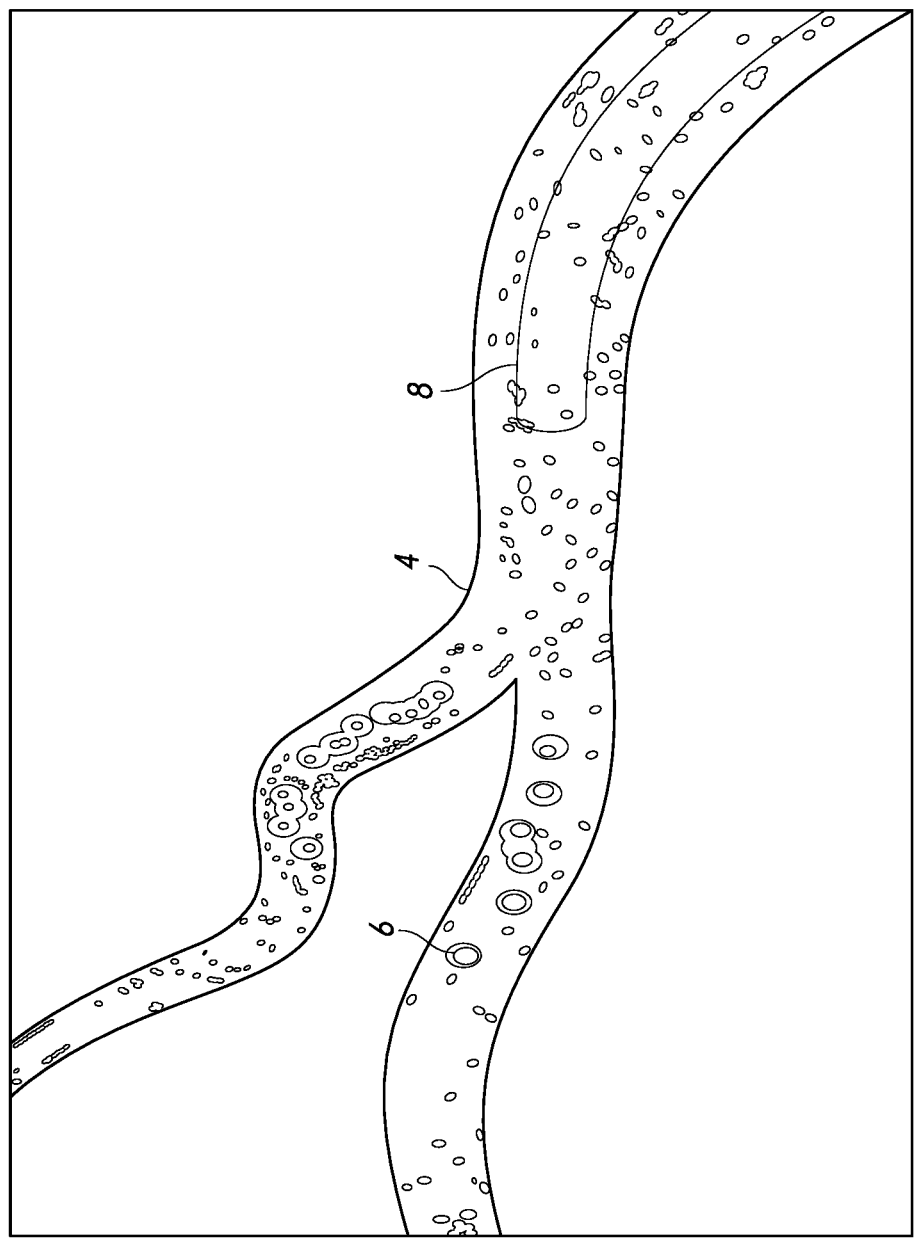
FIG. 1 shows a representation of embolic spheres being released into the arteries that feed the fundus.

A substantial need exists for minimally invasive and cost-effective solutions to improve treatment options and outcomes through the means of small, highly capable, and reliable interventional tools and implants for the reduction, but not total blockage, of blood flow to targeted vascular regions.

Some aspects of the present disclosure provide the means and the methods for utilizing a non-embolic, temporary or permanent, implant that reduces, but does not fully occlude, blood flow in a selected artery and thus mimics the fluid flow reduction of a stretched artery (reduced cross-section and thus reduced fluid flow), resulting in reduced oxygen transport to the targeted tissue.

The implants of the present disclosure shall be constructed of materials compatible with implantation into the body, either singularly or in combination, and assembled into a combined stent and fluid flow restrictor configuration, such that the fluid flow entering into the proximal end of the implant is impeded relative to the natural flow previously existing in the vessel prior to insertion of the implant, thus resulting in a mass flow reduction out of the exit section of the implant into the target organs or tissue distal to the implant location.

The implants described herein may reduce the blood flow by 50% or more, but less than 100%.

In some implementations of the present disclosure, the implant is placed into the vasculature so as to restrict blood flow to the fundus region of the stomach so as to mimic the blood flow reduction normally experienced by the fundus when the stomach is expanded thus impacting Ghrelin levels and reducing the individual's sensation of hunger.

In some implementations of the present disclosure, the implant may be placed into the feeding arteries from aorta to the fundus including the celiac artery, the splenic artery, or other smaller gastric sub branches.

In some implementations of the present disclosure, the implant may be placed into the feeding arteries (e.g., ovarian artery or uterine artery) that provide blood flow to regions of the uterus so as to reduce blood flow to fibroids.

In some implementations of the present disclosure, the implant may be placed into the feeding arteries (e.g., prostate artery) that provide blood flow to the prostate.

The implants described herein may be deployed from a microcatheter having an outer diameter in the range from under 0.027 inches or up to 0.052 inches at the distal working area, and less than 0.052 inches in diameter from the proximal to the distal working area of the delivery system shaft. The microcatheter may be manufactured with polymer, metal and polymer, polymer and thin film, or polymer and integrated braided material for torque control, and may include integrated tether mechanisms or tether lines for release of the implant from the catheter or may utilize the natural self-expansion of the implant materials to facilitate the release. The release may be completed by mechanical energy, or by absorbed energy, or by delivered energy such as thermal or electrical, or by environmental energy leading to natural self-expansion from thermal body temperature transfer to the implant.

The implant diameter after release from the microcatheter may be in the range of 6 mm or less.

Some embodiments of the present disclosure provide a means for restraining, positioning, or recapturing and repositioning of the implant during initial insertion; and optionally repositioning or recapturing the implant for removal after completion of a therapeutically useful time period.

The implant may include a blood flow restrictor that may include thin film, for example constructed of TiNi. At body temperature the thin film TiNi may be in the martensitic (shape memory) state, the austenitic (superelastic) state, or a mixture of both.

In implants including thin film, the thin film may be formed in a substantially planar form and then subsequently shaped into a three dimensional form prior to incorporation into a catheter.

In implants including thin film, the thin film may be formed in a partially three dimensional form and then subsequently further shaped into a final three dimensional form prior to incorporation into a catheter.

In implants including thin film, the thin film may be formed in a substantially three dimensional form prior to incorporation into a catheter.

In implants including thin film, the thin film may be comprised of a regularly repeating pattern of meshed structures, wherein the meshed structures may be any pattern of porosity that optimizes the film's ability to expand from a highly compressed state in the catheter to a substantially expanded state when deployed into the vasculature, while also minimizing the degree of localized stress and strain experienced by elements of the mesh.

In implants including thin film, the thin film may be comprised of a regularly repeating pattern of meshed structures, wherein the meshed structures may be any pattern of porosity that optimizes the occlusive performance of the structure to achieve the desired blood flow reduction.

In implants including thin film, the thin film may be comprised of variable patterns of meshed structures of varying shapes and sizes and spacings, wherein the meshed structures may be any pattern of porosity that optimizes the occlusive performance of the structure to achieve the desired blood flow reduction without creating excessive turbulent flow in the lumen or creating regions of poor circulation that might promote thrombus formation. Pattern variability may include differing porosity between the outer diameter of the structure (closest to the wall of the lumen) and the center of the vessel, non-circular shaped pores, or varying spacial layouts.

In some implants, the thin film structure may be attached to one or more frame portions including braided wire, laser cut, or polymeric elements or combinations thereof. These frame portion(s) may be formed of TiNi, platinum, stainless steel, tantalum, or other metallic or polymeric materials compatible with implantation into the body, either singularly or in combination.

The frame portion(s) may function as the mechanical support for the thin film element(s) during insertion from or retraction back into the catheter and also function to maintain the intended three dimensional shape and position within the vasculature of the thin film flow restricting element(s) during its period of deployment within the blood vessel.

Elements of the implant may function to create radial expansion of the implant assembly upon release from the catheter so as to secure the structure in the vessel with minimal loss of initial positioning.

Elements of the implant may function to facilitate extraction, if needed, with minimal damage to the arterial vessel, including compatibility with the use of existing cardiovascular retrieval methods such as snare devices.

The implants described herein may be constructed from a single element or multiple elements combined by processes such as fusing, bonding, gluing, interweaving, stitching, and sheathing and may include outer material or materials embracing or containing the primary and secondary materials that create the restrictor.

The implants described herein may include similar materials, of metallic or on-metallic composition, where the materials are combined to interact with similar expansion and compression characteristics to facilitate loading into the catheter, release and expansion into the vasculature, and placement and implantation within the arterial system for restriction of blood flow.

The implants described herein also may include dissimilar materials, of metallic and non-metallic composition, where the materials are combined to interact with similar expansion and compression characteristics to facilitate loading into the catheter, release and expansion into the vasculature, and placement and implantation within the arterial system for restriction of blood flow.

Specific elements or coatings on elements may also function to enhance the x-ray contrast of the assembly to aid in visualization and positioning of the device.

The device or portions of the device may be coated with drug eluting materials.

Figure 2:
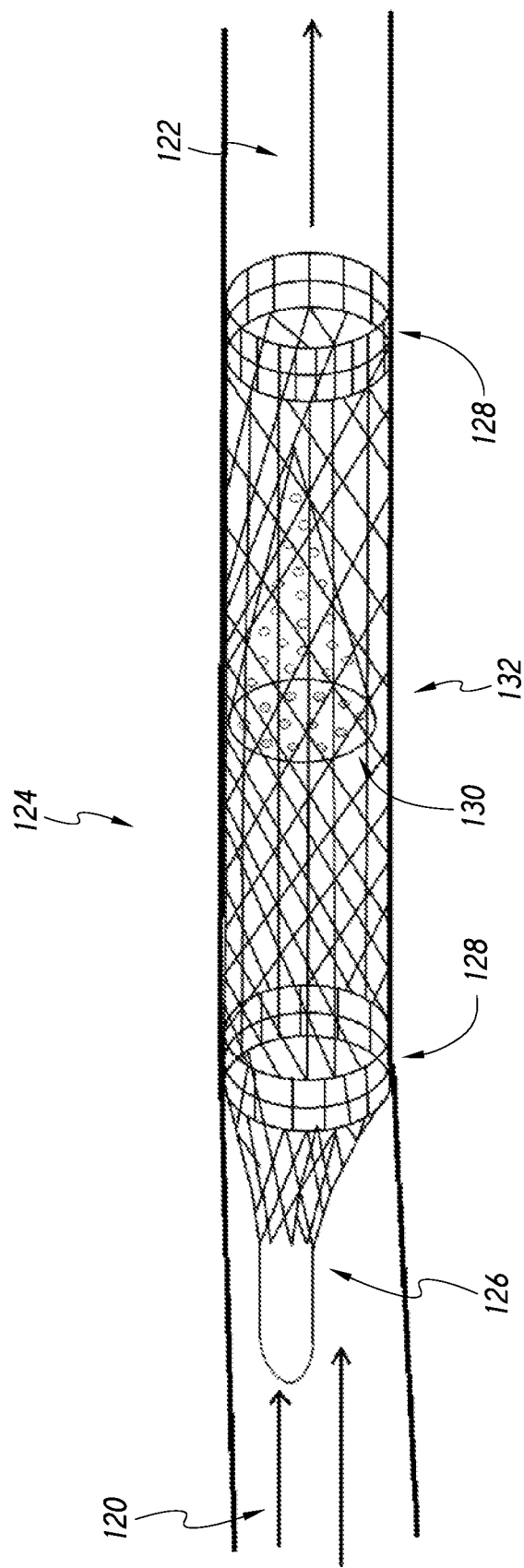
FIG. 2 shows a representation of an implant device positioned into an artery.

FIG. 2 shows a representation of an implant device 124. The implant device 124 includes a frame structure having one or more frame portions 128, 132 that provide mechanical support for one or more flow restricting elements 130, facilitating positioning of the flow restricting element(s) 130 in the artery, locking the flow restricting element 130 in place by radially expanding after release from the catheter to provide sufficient frictional force on the walls of the lumen, and/or providing a structural framework that expands and maintains the intended 3D shape of the flow restricting element 130 due to a greater rigidity of the frame as compared to the flow restriction element(s).

The frame structure may include one or more frame portions 128, 132 that may be of uniform construction or non-uniform construction, for example portions 128, 132 may be of different design. Frame portion 132 may be disposed adjacent a frame portion 128 or between frame portions 128. For example, as shown in FIG. 2, the frame structure may be a cylindrical structure with a central frame portion 132 disposed between frame end portions 128. Frame portions 128, 132 may have different wall patterns, shape, length, and/or diameter. For example, frame portion 128 may be designed to retain the implant device 124 in the vessel, while frame portion 132 may be designed to retain the flow restrictor(s) 130 discussed below. Frame portion(s) 128 may provide greater rigidity and/or permit greater expansion than frame portion 132.

The implant device 124 also includes one or more flow restrictors 130 disposed within a lumen of the frame portion 128 and/or frame portion 132. Flow restrictor 130 may be comprised of a meshed structure, for example a regularly repeating pattern of meshed structures, wherein the meshed structures may be any pattern of porosity that optimizes the occlusive performance of the flow restrictor(s) 130 to achieve the desired blood flow reduction. Multiple elements of flow restrictors 130 may also be used, for example in series. Each flow restrictor 130 may be deployed together with or independently from the frame structure 128, 132.

The flow restrictor 130 may be a fine mesh where the porosity of the mesh (e.g., open area of each pore) may range from about, 50 microns to about 1500 microns, and most ideally about 100 microns to about 1000 microns, e.g., between about 100 microns and about 200 microns, between about 150 microns to about 250 microns, between about 200 microns to about 300 microns, between about 250 microns to about 350 microns, between about 300 microns to about 400 microns, between about 350 microns to about 450 microns, between about 400 microns to about 500 microns, between about 450 microns to about 550 microns, between about 500 microns to about 600 microns, between about 550 microns and about 650 microns, between about 600 microns and about 700 microns, between about 650 microns and about 750 microns, between about 700 microns and about 800 microns, between about 750 microns and about 850 microns, between about 800 microns and about 900 microns, between about 850 microns and about 950 microns, or between about 900 microns and about 1000 microns. The flow restrictor 130 can include a mesh structure for blood flow diversion such that the mesh is of a substantially uniform porosity in the two-dimensional configuration and in the three-dimensional configuration.

The flow restrictor 130 may be constructed of thin film NiTi. The NiTi material may be in the martensitic (shape memory) state, the austenitic (superelastic) state, a mixture of both, or may be a multilayer of several film compositions. Thin film NiTi is durable and allows for controlled porosity. The thin film components of the implant described herein can be formed from a continuous or monolithic sheet (e.g., thin film layer). The continuous or monolithic sheet can have a substantially uniform thickness. The thickness can be less than or equal to 0.005 inches, less than or equal to 0.003 inches, less than or equal to 0.002 inches, or less than or equal to 0.001 inches.

The implant device 124 may also include an interfacing element 126 extending from the frame structure. Interfacing element 126 represents a connective element used to facilitate release of the device from the catheter and also for repositioning or recapture if needed. In the orientation shown, blood flow 120 enters the implant device 124 and is reduced due to the fluid impedance of the flow restrictor so that the blood flow out of the device 122 is reduced, but not fully occluded, relative to the natural flow in the artery prior to device insertion.

Figure 3A:
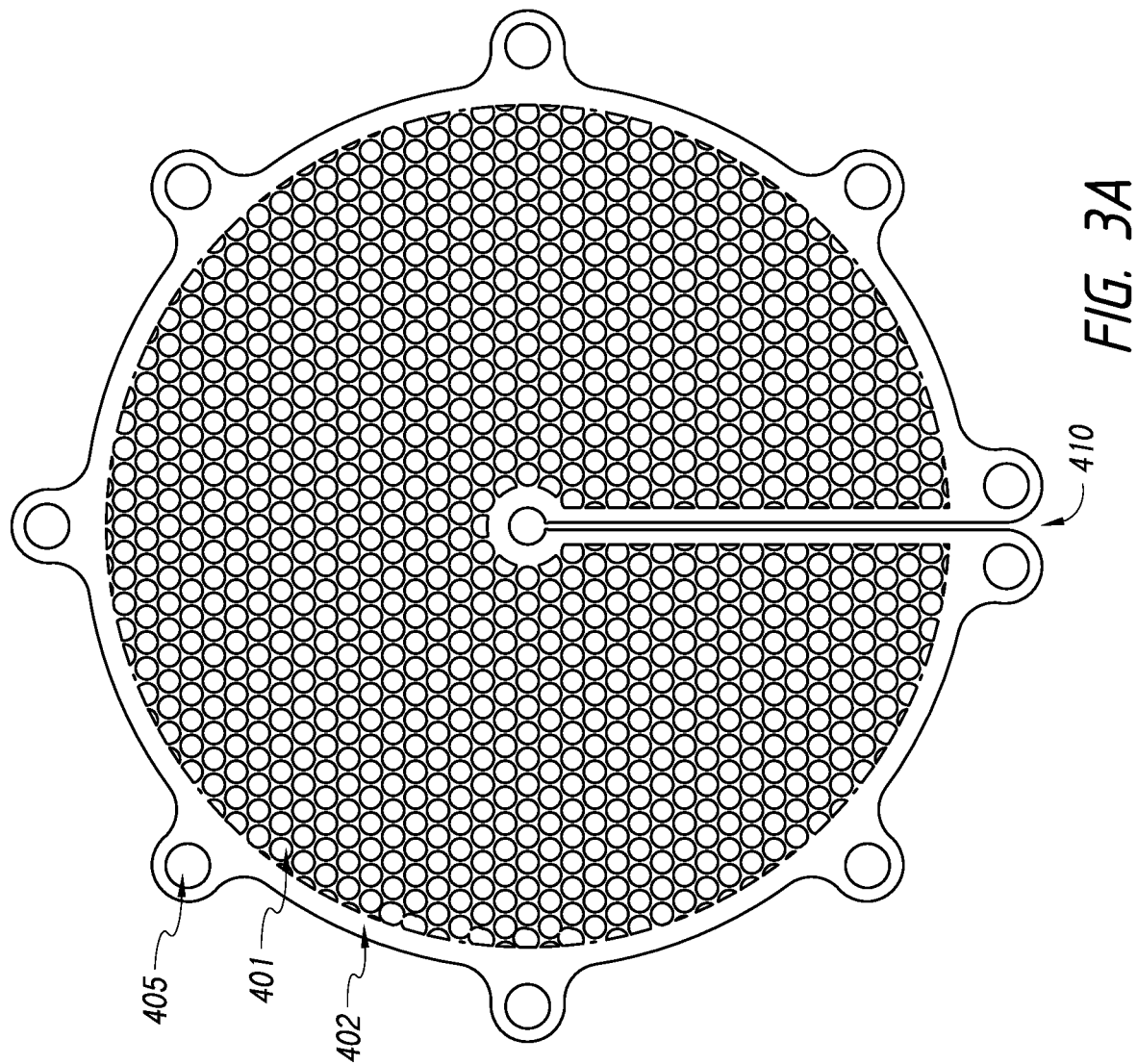
FIGS. 3A-3C show an example of one type of thin film flow restricting element.
Figure 3B:
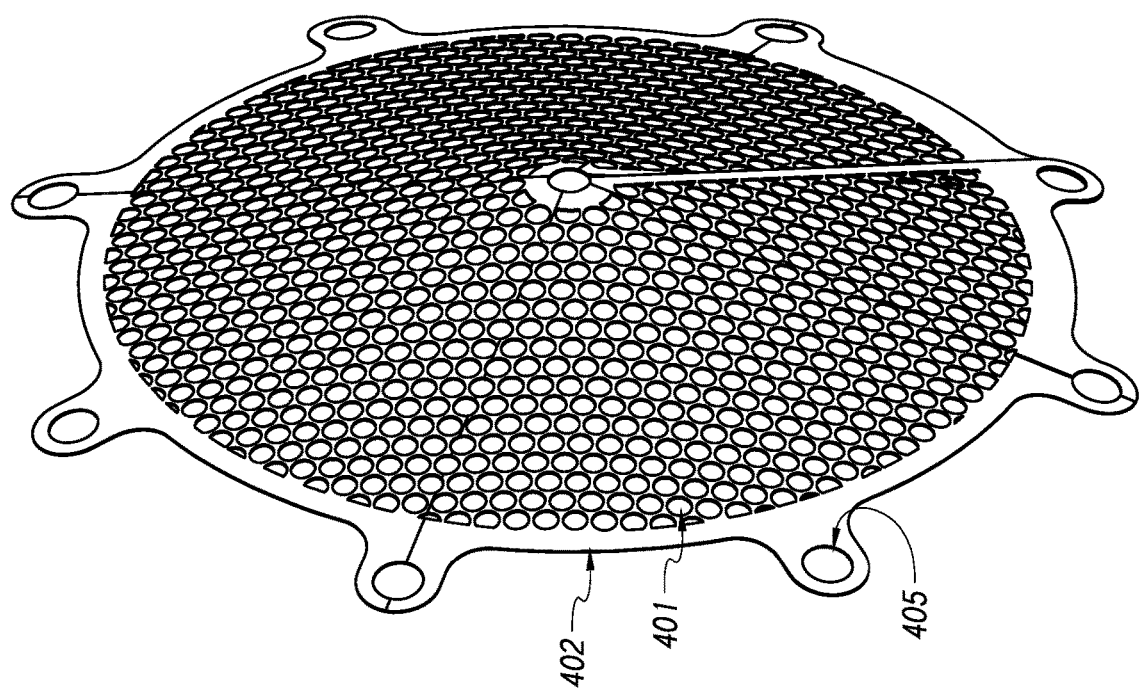
Figure 3C:
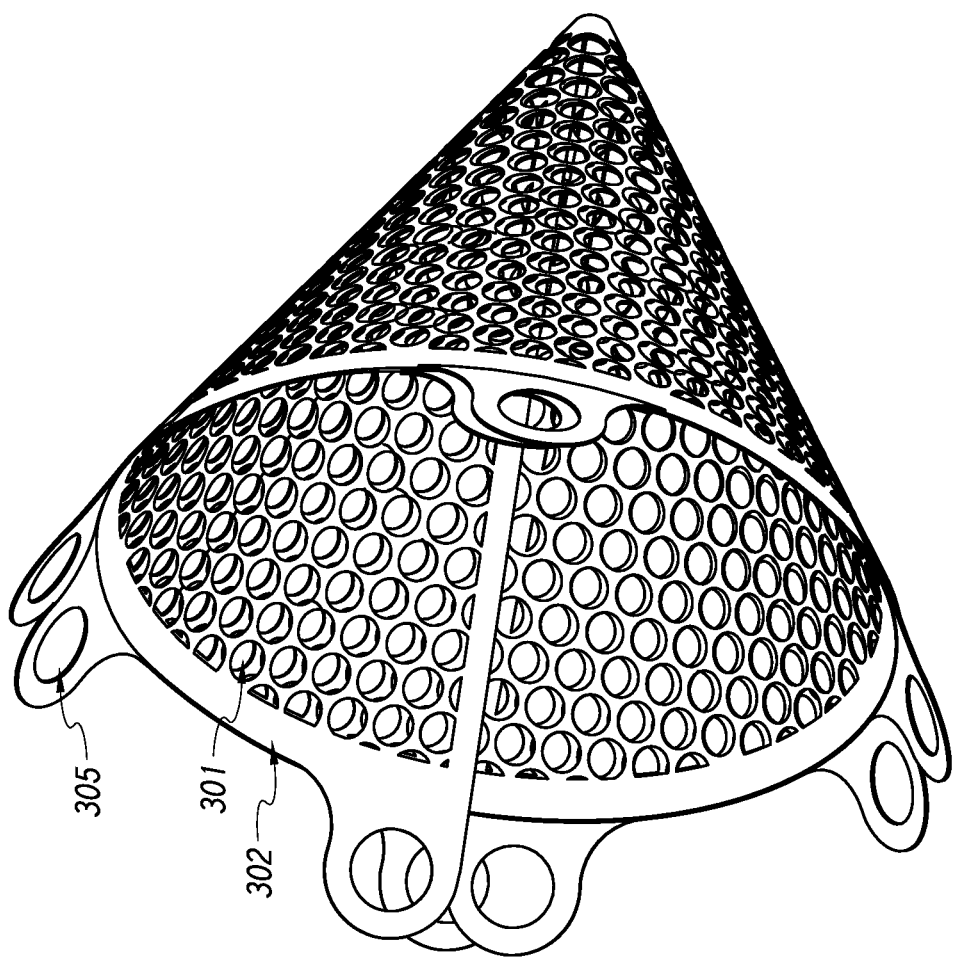

FIGS. 3A-3C illustrate a flow restrictor 130 that may be used with any of the implant devices described herein. As illustrated, the flow restrictor 130 can transition between a first, deployed configuration (FIG. 3B) and a second, collapsed configuration (FIG. 3C) with a reduced overall diameter compared to the first configuration. The flow restrictor 130 is in the collapsed configuration for delivery and then transitions to the deployed configuration when released from the delivery catheter, for example within the one or more frame portions 128, 130. In the deployed configuration, the flow restrictor 130 can reduce fluid flow through the vessel without completely occluding fluid flow.

FIG. 3A shows an example of flow restricting element 130 in its 2D planar form. The restricting element 130 can include a sheet of material with pores 401. The restricting element can include an outer solid rim 402 without any pores. The flow restrictor 130 may be coupled to the frame 128, 130, for example using one or more attachment structures, such as grommets 405, at a periphery of the flow restricting element 130. The grommets can be attached to the frame by, for example, threading with wire or similar elements. The size, placement, and density of pores 401 can be any arrangement giving the desired flow reduction. A slot 410 may extend from an outer periphery of the flow restricting element 130 toward a center region of the flow restricting element 130 to enable wrapping on the element for insertion into the catheter (see FIGS. 3B and 3C). In the collapsed configuration, the outer periphery of the flow restrictor forms a first end of the flow restrictor and the central region forms a second end of the flow restrictor.

FIG. 3B shows how, by overlapping the two sides of slot 410, the element of FIG. 3A can be modified into a 3D shape with a slight conical profile, and FIG. 3C shows a more significant wrapping to give a tighter conical profile with a reduced outer diameter such as would be needed for insertion into a small diameter catheter. In the deployed configuration, a first side of the slot 410 at least partially overlap a second side of the slot 410 by a first distance to prevent fluid from flowing through the slot 410. In the collapsed configuration, the first side of the slot 410 may overlap the second slot 410 by a second distance that is greater than the first distance to reduce the overall diameter of the flow restrictor.

Although the frame structure 128, 132 shown in FIG. 1 has a substantially cylindrical shape, the frame structure 128, 132 can take on any configuration. For example, the frame structure 128, 132 may be braided or laser cut.

Figure 4:
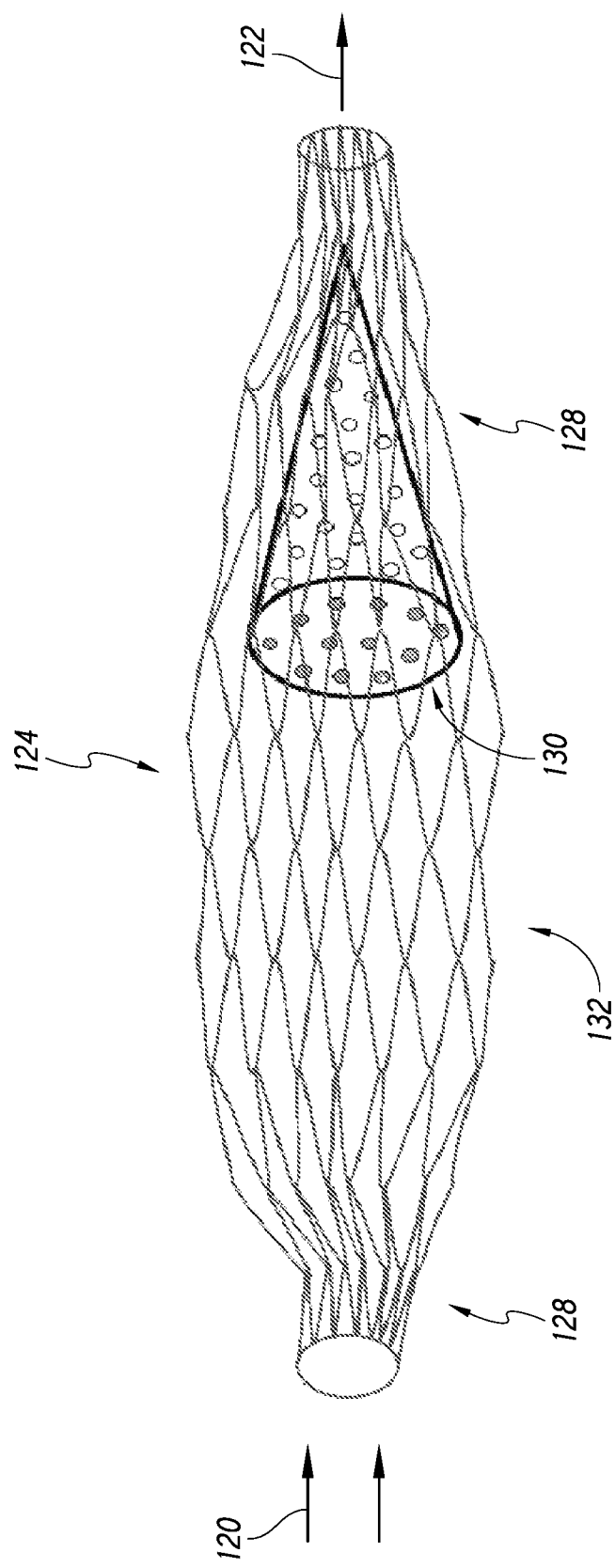
FIG. 4 shows another implant device.

FIG. 4 illustrates another implant device 124 that may include any of the features described above with respect to the figures above. As shown, the frame structure of the implant device 124 has an enlarged central region 132 compared to one or both end portions 128. The enlarged central region 132 locates the implant device 124 in the vessel. The flow restrictor 130 can be centered or positioned off center and closer to an end portion 128 of the frame structure. A proximal portion of the flow restrictor 130 may be disposed within the enlarged central region 132, while a distal portion of the flow restrictor is positioned within the end portion 128. The frame portions 128, 132 can include a plurality of undulating rings, each ring having peaks and valleys.

Methods of implanting the flow restrictor may include one or more of the following features:

1. Method of reducing but not fully blocking blood flow from supply points of the aortic artery into targeted tissue, organ or glandular regions by the use of an integrated implant.
2. Method utilizing a femoral or radial access system to implant an acute to long term flow restrictor, used singularly or at multiple locations, positioned in the vascular system between the aortic artery and smaller distal vessels to achieve a restriction in blood flow from the vessel standard flow and deprive full oxygenation to the distal sections of the arteries and glands and organs, manifesting in a similar response as when the arteries are stretched by the expansion of the elastic section of the fundus thus impacting the communication to the body of the hunger feeling.
3. Method embodying the use of a femoral or radial access system to retrieve the implanted flow restriction apparatus for removal in guidance with suppression or non-suppression of the hunger response
4. A femoral or radial access catheter based delivery system carrying a flow restricting device that impedes the glandular effectiveness of the fundus to signal hunger through chemical or electrical stimulus to the body thus reducing the sensation of hunger.
5. An implant made from acceptable implant materials of polymer, metallic or a combination of both, that can reduce but not fully block blood flow from the connected portion of the aortic artery to the sub capillary vessels, without initiating a cellular reaction of de-oxygenation or tissue degradation.
6. An implant delivered by standard catheterization procedures where the catheter encloses one or more implants and is able to access a desired position in the vasculature for placement and then release of the implant or implants.

Although certain methods of use have been described herein in connection with the fundus region, the implants described herein can be used in the other regions of the body, including the uterine region to treat fibroids or vessels adjacent the prostate region.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially planar" includes "planar" and within 5 degrees of planar.

Example Embodiments

The following example embodiments identify some possible permutations of combinations of features disclosed herein, although other permutations of combinations of features are also possible.

1. An implantable device comprising:
 a frame comprising a central portion and an end portion on either end of the frame,
 a flow restrictor disposed within a lumen of the frame, the flow restrictor configured to transition between a collapsed configuration and a deployed configuration, the flow restrictor comprising a porosity configured to reduce fluid flow through the flow restrictor without completely occluding fluid flow.

2. The implantable device of Embodiment 1, wherein the flow restrictor comprises nitinol.

3. The implantable device of Embodiment 1 or 2, wherein the flow restrictor is coupled to the frame.

4. The implantable device of Embodiment 3, wherein the flow restrictor comprises one or more grommets configured to couple the flow restrictor to the frame.

5. The implantable device of any one of the preceding Embodiments, wherein, in the deployed configuration, an entire outer periphery of the flow restrictor comprises no porosity.

6. The implantable device of any one of the preceding Embodiments, wherein the central portion of the frame comprises a first wall pattern and at least one of the end portions comprises a second wall pattern different from the first wall pattern.

7. The implantable device of any one of the preceding Embodiment, wherein the flow restrictor is configured to transition between a substantially planar state and a three-dimensional state the collapsed configuration, the flow restrictor comprising an outer periphery and a central region in the substantially planar state.

8. The implantable device of Embodiment 7, wherein in the substantially planar configuration, the flow restrictor comprises a slot defined by a first edge and a second edge, the slot extending from the outer periphery of the flow restrictor toward the center region of the flow restrictor, and wherein in the collapsed configuration, the first edge overlaps the second edge by a first distance to reduce an outer diameter of the flow restrictor.

9. The implantable device of Embodiment 8, wherein in the deployed configuration, the first edge overlaps the second edge by a second distance that is less than the first distance.

10. The implantable device of any one of Embodiments 7 to 9, wherein in the collapsed configuration, the outer periphery of the flow restrictor forms a first end of the flow restrictor and the central region forms a second end of the flow restrictor.

11. The implantable device of any one of the preceding Embodiments, wherein the flow restrictor comprises a first end and a second end, the first end having a greater diameter than the second end in the collapsed configuration.

12. The implantable device of any one of the preceding Embodiments, wherein a wall thickness of the flow restrictor is different from a wall thickness of the frame.

13. The implantable device of any one of the preceding Embodiments, wherein the central portion of the frame has an enlarged diameter compared to either end portion of the frame.

14. The implantable device of any one of the preceding Embodiments, wherein the frame is cylindrical in the deployed configuration.

15. The implantable device of any one of the preceding Embodiments, wherein the flow restrictor comprises a monolithic film having the porosity.

16. A method of suppressing hunger sensation, the method comprising:
 advancing an implantable device to a fundus region of the stomach;
 expanding the implantable device within the fundus region, the implantable device comprising a flow restrictor; and
 reducing fluid flow through the fundus region using the expanded implantable device.

17. The method of Embodiment 16, wherein the implantable device comprises nitinol.

18. The method of Embodiment 16 or 17, wherein the implantable device comprises a frame configured to support the flow restrictor.

19. A method of treating fibroids in a uterus, the method comprising:
 advancing an implantable device to an artery that provides blood flow to the uterus;
 expanding the implantable device within the artery, the implantable device comprising a flow restrictor; and
 reducing fluid flow to the uterus using the expanded implantable device.

20. The method of Embodiment 19, wherein the implantable device comprises nitinol.

21. The method of Embodiment 19 or 20, wherein the implantable device comprises a frame configured to support the flow restrictor.

22. A method of treating an enlarged prostate, the method comprising:
 advancing an implantable device within an artery that provides blood flow to the prostate;
 expanding the implantable device within the artery, the implantable device comprising a flow restrictor; and
 reducing fluid flow through the artery using the expanded implantable device.

23. The method of Embodiment 22, wherein the implantable device comprises nitinol.

24. The method of Embodiment 22 or 23, wherein the implantable device comprises a frame configured to support the flow restrictor.

The following is claimed:

1. An implantable device comprising:
 a frame comprising a central portion and an end portion on either end of the frame; and
 a flow restrictor disposed within a lumen of the frame between the end portions, the flow restrictor being made of a monolithic film comprising nitinol, the flow restrictor configured to transition between a collapsed configuration and a deployed configuration, the flow restrictor comprising a porosity configured to reduce fluid flow through the flow restrictor without completely occluding fluid flow,
 wherein the flow restrictor comprises a first end and a second end, the first end having a greater diameter than that of the second end in the collapsed configuration.

2. The implantable device of claim 1, wherein the flow restrictor is coupled to the frame.

3. The implantable device of claim 2, wherein the flow restrictor comprises one or more grommets configured to couple the flow restrictor to the frame.

4. The implantable device of claim 2, wherein the flow restrictor is coupled to the frame by threading one or more attachment structure of the flow restrictor to the frame.

5. The implantable device of claim 1, wherein, in the deployed configuration, an entire outer periphery of the flow restrictor comprises no porosity.

6. The implantable device of claim 1, wherein the central portion of the frame comprises a first wall pattern configured to provide a first rigidity for the central portion, and at least one of the end portions comprises a second wall pattern configured to provide a second rigidity for the end portion different from the first rigidity provided by the first wall pattern.

7. The implantable device of claim 1, wherein in a substantially planar state the flow restrictor comprising an outer periphery and a central region, and wherein the flow restrictor comprises a slot defined by a first edge and a second edge, the slot extending from the outer periphery of the flow restrictor toward the central region of the flow restrictor.

8. The implantable device of claim 7, wherein in the collapsed configuration, the first edge overlaps the second edge by a first distance to reduce an outer diameter of the flow restrictor.

9. The implantable device of claim 8, wherein in the deployed configuration, the first edge overlaps the second edge by a second distance that is less than the first distance.

10. The implantable device of claim 7, wherein in the collapsed configuration, the outer periphery of the flow restrictor forms a first end of the flow restrictor and the central region forms a second end of the flow restrictor.

11. The implantable device of claim 1, wherein a wall thickness of the flow restrictor is different from a wall thickness of the frame.

12. The implantable device of claim 1, wherein the central portion of the frame has an enlarged diameter compared to either end portion of the frame.

13. The implantable device of claim 1, wherein the frame is cylindrical in the deployed configuration.

14. The implantable device of claim 1, wherein the flow restrictor is braided or laser cut.

15. A method of suppressing hunger sensation, the method comprising:

advancing an implantable device to a fundus region of the stomach, the implantable device comprising a frame, having a central portion and end portions on either end of the frame, and a flow restrictor disposed within a lumen of the frame between end portions;

wherein the flow restrictor is made of a porous monolithic film comprising nitinol, the flow restrictor comprising a first end and a second end, the first end having a greater diameter than the second end in a collapsed configuration; expanding the implantable device within the fundus region;

and reducing, without completely occluding, fluid flow through the fundus region using the porous monolithic film of the flow restrictor of the implantable device, in an expanded configuration.

* * * * *